United States Patent [19]

Henrick et al.

[11] 4,252,724

[45] Feb. 24, 1981

[54] NOVEL COMPOSITIONS

[75] Inventors: Clive A. Henrick, Palo Alto; Barbara A. Garcia, Boulder Creek, both of Calif.

[73] Assignee: Zoecon Corporation, Palo Alto, Calif.

[21] Appl. No.: 66,264

[22] Filed: Aug. 13, 1979

Related U.S. Application Data

[63] Continuation-in-part of Ser. No. 878,091, Feb. 16, 1978, which is a continuation-in-part of Ser. No. 824,947, Aug. 15, 1977, which is a continuation-in-part of Ser. No. 779,886, Mar. 21, 1977.

[51] Int. Cl.³ .......................................... C07D 207/327
[52] U.S. Cl. ........................... 260/326.43; 260/326.36; 71/95

[58] Field of Search ....................... 260/326.43, 326.36

[56] References Cited

U.S. PATENT DOCUMENTS

| | | | |
|---|---|---|---|
| 4,032,658 | 6/1977 | Beregi | 424/309 |
| 4,212,879 | 7/1980 | Ohsumi et al. | 260/326.43 |

*Primary Examiner*—Mary C. Lee
*Attorney, Agent, or Firm*—Donald W. Erickson; Thomas T. Gordon

[57] ABSTRACT

Benzylpyrrolylmethyl esters and thiolesters of amino acids, intermediates therefor, synthesis thereof and the use of said esters and thiolesters and compositions for the control of pests.

19 Claims, No Drawings

NOVEL COMPOSITIONS

This is a continuation-in-part of Ser. No. 878,091, filed Feb. 16, 1978 which is, in turn, a continuation-in-part of Ser. No. 824,947, filed Aug. 15, 1977 and Ser. No. 779,886, filed Mar. 21, 1977, the entire disclosures of which are incorporated herein by reference.

This invention relates to novel esters and thiolesters of amino acids, novel intermediates therefor, synthesis thereof, and the control of pests.

The esters and thiolesters of the present invention are represented by the following formula (A):

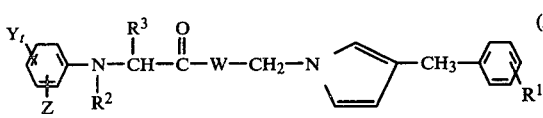

wherein, $R^1$ is hydrogen, fluoro, bromo, chloro, trifluoromethyl, methyl, methoxy or methylthio;
W is oxygen or sulfur;
t is zero, one, two, three or four;
Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
Z is independently selected from the values of Y, cycloalkyl and lower haloalkoxy; or Y and Z together form a methylenedioxy group;
$R^2$ is hydrogen, lower alkyl, lower haloalkylcarbonyl, or formyl;
$R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms or lower cycloalkyl of 3 or 4 carbon atoms; and the salt thereof of a strong inorganic acid or organic acid.

The compounds of the present invention represented by formula (A) are useful agents for the control of pests such as insects and acarids.

In the description hereinafter and the appended claims, each of $R^1$, $R^2$, $R^3$, W, Y, Z and t is as defined hereinabove, unless otherwise specified.

The compounds of formula (A) wherein W is oxygen can be synthesized as outlined below.

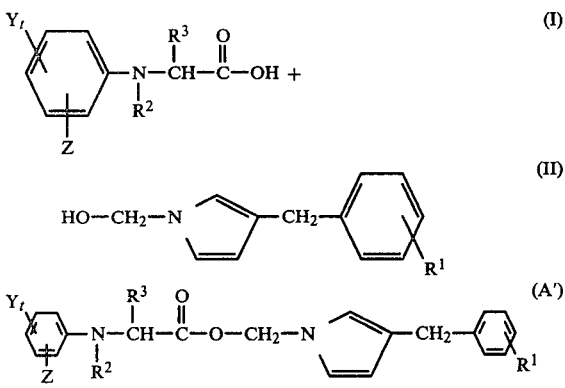

In the general practice of the above synthesis, an acid, salt thereof or the acid chloride is reacted with an alcohol of formula II to form the carboxylic ester A'. For example, an acid chloride of the acid of formula I is reacted with an alcohol of formula II in an organic solvent such as diethyl ether in the presence of triethylamine. In another embodiment, the esters of formula A' are synthesized by reaction of an acid of formula I with phosgene in the presence of an ether such as 1,4-dioxane to form the corresponding oxazolidine-2,5-dione, which is then reacted with an alcohol of formula II to make the corresponding ester of formula A'. In another synthesis, the acid of formula I or salt thereof is reacted with the bromide, chloride or mesylate of the alcohol of formula II to form an ester of formula A'. The starting materials of formula I are described by Henrick and Garcia, Offenlegungsschrift 28 12 169. The alcohols of formula II can be made as described by Ohoumi et al., Offenlegungsschrift No. 28 43 760.

In another embodiment, the compounds of formula (A) can be prepared by the reaction of an amine (III) with an α-halo ester of formula IV (X is bromo or chloro).

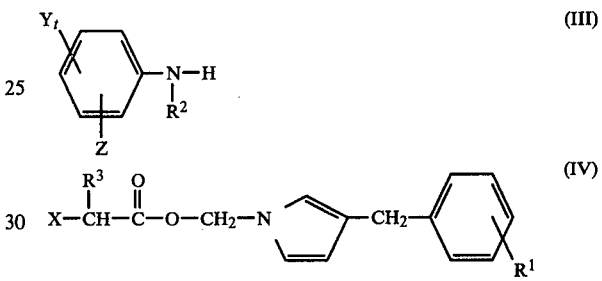

The reaction of an amine (III) and halo ester (IV) is generally carried out neat or in an organic solvent such as hexamethylphosphorictriamide, tetrahydrofuran, dimethylformamide, dimethylsulfoxide, or the like. The halo esters of formula IV can be prepared by reaction of an acid halide thereof with an alcohol of formula II.

The thiolesters of formula (A) can be prepared by the reaction of, for example, the sodium salt of a thioacid corresponding to formula I with the bromide or mesylate of the alcohol of formula II.

The following terms, wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers to an alkyl group substituted with one to three halogen atoms such as chloromethyl, fluoromethyl, trifluoromethyl, 2,2,2,-trifluoroethyl, 6-chlorohexyl, 2-fluoroethyl, and the like. The term "lower alkoxy" refers to an alkoxy group, straight or branched, having a chain length of one to eight carbon atoms. The term "lower alkylthio" refers to an alkylthio group, straight or branched, having a chain length of one to eight carbon atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of two to eight carbon atoms. The term "lower haloalkenyloxy" refers to a lower alkenyloxy group substituted with one to three halogen atoms.

The term "cycloalkyl" refers to a cycloalkyl group of three to eight cyclic carbon atoms. The term "cycloalkalkyl" refers to a cycloalkyl group wherein one hydrogen atom is replaced by a lower alkyl group, the total number of carbon atoms being from four to twelve, such a cyclopropanemethyl, cyclobutaneethyl, cyclohexanemethyl, and the like.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula (A) herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g., propoxur, carbaryl, diazinon, naled, dichlorvos, phosmet, chlorpyrifos, acephate, methoprene, kinoprene, hydroprene, cyhexatin, resmethrin, permethrin and fenvalerate.

The following examples are provided to illustrate the practice of the present invention. Temperature is given in degrees Centigrade. RT means room temperature. The term 3-benzylpyrrolylmethyl means 3-benzyl-1-pyrrolylmethyl, as shown in formula (A).

EXAMPLE 1

To a stirred solution of 3-benzylpyrrolylmethyl alcohol (0.99 mmol) and triethylamine (0.14 g, 1.38 mmol) in ether (about 15 ml), under nitrogen, is added by syringe a solution of the acid chloride of N-(2-chloro-4-trifluoromethylphenyl)valine (1.5 mmol) in ether. The mixture is stirred for 30 minutes and then quenched with saturated aqueous sodium bicarbonate. The ether phase is washed with aqueous sodium bicarbonate, water and brine and filtered through silica. Evaporation of solvent, followed by thin layer chromatography using a circular chromatography, eluting with 20% ether/hexane, gives the 3-benzylpyrrolylmethyl ester of N-(2-chloro-4-trifluoromethylphenyl)valine, [3-benzylpyrrolylmethyl 2-(2-chloro-4-trifluoromethylphenylamino)-3-methylbutanoate].

EXAMPLE 2

To the acid chloride of 2-(2-fluoro-4-trifluoromethylphenylamino)-3-methylbutanoic acid (2.5 mmol) in ether is added 1.3 ml of triethylamine followed by 3-benzylpyrrolylmethyl alcohol (2.0 mmol) in ether over about 2 minutes. The reaction mixture is stirred for about 18 hours and then quenched with saturated aqueous sodium bicarbonate. The organic phase is washed with aqueous sodium bicarbonate, water and brine, dried over calcium sulfate and solvent evaporated. The crude product is chromatographed on a circular chromatograph eluting with 20% ether/hexane to give 3-benzylpyrrolylmethyl 2-(2-fluoro-4-trifluoromethylphenylamino)-3-methylbutanoate.

EXAMPLE 3

To a stirred solution of 3-benzylpyrrolylmethyl alcohol (1.8 mmol), 2-(2-methyl-4-trifluoromethylphenylamino)-3-methylbutanoic acid (2.0 mmol) and 4-dimethylaminopyridine (0.65 mmol) in 20 ml of methylene chloride and 2 ml of dimethylformamide is added N,N'-dicyclohexylcarbodiimide (2.0 mml). The reaction mixture is stirred, under nitrogen, for two hours and then filtered and extracted with water. The aqueous phase is extracted with ether. The combined organic phases are washed with saturated aqueous sodium bicarbonate, water and saturated aqueous sodium chloride, dried over calcium sulfate and solvent evaporated. The crude product is chromatographed on a rotary chromatograph eluting with 25% ether/hexane to yield 3-benzylpyrrolylmethyl 2-(2-methyl-4-trifluoromethylphenylamino)-3-methylbutanoate.

EXAMPLE 4

To a solution of 3-(4-chlorophenyl)-4-isopropyloxazolidine-2,5-dione (336 mg, 1.32 mmol) and 4-dimethylaminopyridine in 5 ml of dry tetrahydrofuran is added a solution of 3-benzylpyrrolylmethyl alcohol (1.26 mmol) in 3 ml of dry tetrahydrofuran. The reaction mixture is stirred for about 20 hours, under dry air, and then diluted with ether followed by washing with saturated aqueous sodium bicarbonate, water and saturated aqueous sodium chloride. After drying over calcium sulfate, solvent is evaporated. The crude product is chromatographed on a rotary chromatograph eluting with 15% ether/hexane to give 3-benzylpyrrolylmethyl 2-(4-chlorophenylamino)-3-methylbutanoate.

Following the above procedure, 3-(4-methylphenyl)-4-isopropyloxazolidine-2,5-dione is reacted with 3-benzylpyrrolylmethyl alcohol to give 3-benzylpyrrolylmethyl 2-(4-methylphenylamino)-3-methylbutanoate.

In the same way, 3-(4-trifluoromethylphenyl)-4-isopropyloxazolidine-2,5-dione is reacted with 3-benzylpyrrolylmethyl alcohol to give 3-benzylpyrrolylmethyl 2-(4-trifluoromethylphenylamino)-3-methylbutanoate.

EXAMPLE 5

Using the procedure of Example 3, each of the acids, N-(4-chloro-2-fluorophenyl)valine, N-(3-fluoro-4-methylphenyl)-valine, N-(2-fluoro-4-methylphenyl)valine, N-(2,4-dichlorophenyl)valine, N-(4-bromo-2-fluorophenyl)valine, and N-(2-chloro-4-methylphenyl)valine is reacted with 3-benzylpyrrolylmethyl alochol to yield the respective ester:

3-benzylpyrrolyl ester of N-(4-chloro-2-fluorophenyl)-valine
3-benzylpyrrolyl ester of N-(3-fluoro-4-methylphenyl)-valine
3-benzylpyrrolyl ester of N-(2-fluoro-4-methylphenyl)-valine
3-benzylpyrrolyl ester of N-(2,4-dichlorophenyl)valine
3-benzylpyrrolyl ester of N-(4-bromo-2-fluorophenyl)-valine
3-benzylpyrrolyl ester of N-(2-chloro-4-methylphenyl)-valine

EXAMPLE 6

The acid 2-(4-fluorophenylamino)-3-methylbutanoic acid is reacted with 3-benzylpyrrolylmethyl alcohol using the procedure of Example 3 to give 3-benzylpyrrolylmethyl 2-(4-fluorophenylamino)-3-methylbutanoate.

In the same way, using the procedure of Example 3, each of the acids under col. I is converted to the ester under col. II by reaction with 3-benzylpyrrolylmethyl alcohol.

I 2-(4-methoxyphenylamino)-3-methylbutanoic acid
2-(4-bromophenylamino)-3-methylbutanoic acid
2-(4-t-butylphenylamino)-3-methylbutanoic acid
2-(4-ethylphenylamino)-3-methylbutanoic acid
2-phenylamino-3-methylbutanoic acid
2-(4-methylthiophenylamino)-3-methylbutanoic acid
2-(4-cyclopropylphenylamino)-3-methylbutanoic acid

II 3-benzylpyrrolylmethyl 2-(4-methoxyphenylamino)-3-methylbutanoate
3-benzylpyrrolylmethyl 2-(4-bromophenylamino)-3-methylbutanoate
3-benzylpyrrolylmethyl 2-(4-t-butylphenylamino)-3-methylbutanoate
3-benzylpyrrolylmethyl 2-(4-ethylphenylamino)-3-methylbutanoate
3-benzylpyrrolylmethyl 2-phenylamino-3-methylbutanoate
3-benzylpyrrolylmethyl 2-(4-methylthiophenylamino)-3-methylbutanoate
3-benzylpyrrolylmethyl 2-(4-cyclopropylphenylamino)-3-methylbutanoate

EXAMPLE 7

The acid chloride of 2-(2-chloro-4-trifluoromethylphenylamino)-3-methylbutanoic acid is reacted with 3-(4-fluorobenzyl)-pyrrolylmethyl alcohol in ether as in Example 1 to give 3-(4-fluorobenzyl)-pyrrolylmethyl 2-(2-chloro-4-trifluoromethylphenylamino)-3-methylbutanoate.

EXAMPLE 8

The acid chloride of 2-(2-fluoro-4-trifluoromethylphenylamino)-3-methylbutanoic acid is reacted with 3-(3-fluorobenzyl)-pyrrolylmethyl alcohol using the procedure of Example 1 to give 3-(3-fluorobenzyl)-pyrrolylmethyl 2-(2-fluoro-4-trifluoromethylphenylamino)-3-methylbutanoate.

EXAMPLE 9

The alcohols 3-(4-methoxybenzyl)-pyrrolylmethyl alcohol and 3-(3-methylbenzyl)-pyrrolylmethyl alcohol are each reacted with 2-(2-fluoro-4-trifluoromethylphenylamino)-3-methylbutanoic acid to yield 3-(4-methoxybenzyl)-pyrrolylmethyl 2-(2-fluoro-4-trifluoromethylphenylamino)-3-methylbutanoate and 3-(3-methylbenzyl)-pyrrolylmethyl 2-(2-fluoro-4-trifluoromethylphenylamino)-3-methylbutanoate, respectively.

EXAMPLE 10

Each of the alcohols, 3-(3-methoxybenzyl)-pyrrolylmethyl alcohol and 3-(3-chlorobenzyl)-pyrrolylmethyl alcohol, is reacted with 2-(2-fluoro-4-trifluoromethylphenylamino)-3-methylbutanoic acid using the procedure of Example 3 to yield 3-(3-methoxybenzyl)-pyrrolylmethyl 2-(2-fluoro-4-trifluoromethylphenylamino)-3-methylbutanoate and 3-(3-chlorobenzyl)pyrrolylmethyl 2-(2-fluoro-4-trifluoromethylphenylamino)-3-methylbutanoate.

What is claimed is:

1. A compound of the formula (A):

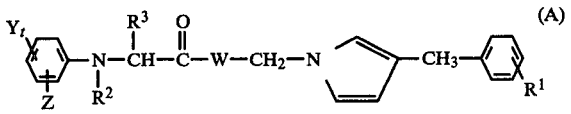

wherein,
- $R^1$ is hydrogen, fluoro, bromo, chloro, trifluoromethyl, methyl, methoxy or methylthio;
- W is oxygen or sulfur;
- t is zero, one, two, three or four;
- Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
- Z is independently selected from the values of Y, cycloalkyl and lower haloalkoxy; or Y and Z together form a methylenedioxy group;
- $R^2$ is hydrogen, lower alkyl, lower haloalkylcarbonyl, or formyl;
- $R^3$ is lower alkyl of 2 to 5 carbon atoms, lower alkenyl of 2 to 5 carbon atoms, lower haloalkyl of 1 to 4 carbon atoms, lower haloalkenyl of 2 to 4 carbon atoms or lower cycloalkyl of 3 or 4 carbon atoms; and the salt thereof of a strong inorganic acid or organic acid.

2. A compound according to claim 1 wherein W is oxygen, $R^2$ is hydrogen or methyl, and $R^3$ is isopropyl.

3. A compound according to claim 2 wherein Y is hydrogen, bromo, chloro, fluoro, lower alkyl of 1 to 4 carbon atoms, trifluoromethyl, lower alkoxy of 1 to 2 carbon atoms or lower alkylthio of 1 to 2 carbon atoms; Z is hydrogen or independently selected from the values of Y; and t is zero or one.

4. A compound according to claim 3 wherein Z is hydrogen.

5. A compound according to claim 3 wherein Z is hydrogen and Y is in the para position.

6. A compound according to claim 5 wherein $R^2$ is hydrogen and t is one.

7. A compound according to claim 6 wherein $R^1$ is hydrogen.

8. A compound according to claim 6 wherein $R^1$ is in the para position and $R^1$ is fluoro.

9. A compound according to claim 6 wherein $R^1$ is in the meta position and $R^1$ is fluoro.

10. A compound according to claim 3 wherein t is one, Y is in the ortho position and Z is in the para position.

11. A compound according to claim 10 wherein Z is trifluoromethyl.

12. A compound according to claim 11 wherein $R^2$ is hydrogen and Y is hydrogen, chloro or fluoro.

13. A compound according to claim 12 wherein $R^1$ is hydrogen.

14. A compound according to claim 12 wherein $R^1$ is in the para position.

15. A compound according to claim 12 wherein $R^1$ is in the meta position.

16. A compound according to claim 14 wherein $R^1$ is fluoro.

17. A compound according to claim 15 wherein $R^1$ is fluoro.

18. A compound according to claim 8 wherein $R^1$ is fluoro.

19. A compound according to claim 9 wherein $R^1$ is fluoro.

* * * * *